US009128102B2

(12) United States Patent
Krizman et al.

(10) Patent No.: US 9,128,102 B2
(45) Date of Patent: Sep. 8, 2015

(54) HER3 PROTEIN SRM/MRM ASSAY

(71) Applicants: David Krizman, Gaithersburg, MD (US); Todd Hembrough, Gaithersburg, MD (US); Sheeno Thyparambil, Frederick, MD (US)

(72) Inventors: David Krizman, Gaithersburg, MD (US); Todd Hembrough, Gaithersburg, MD (US); Sheeno Thyparambil, Frederick, MD (US)

(73) Assignee: EXPRESSION PATHOLOGY, INC., Rockville, MD (US)

( * ) Notice: Subject to any disclaimer, the term of this patent is extended or adjusted under 35 U.S.C. 154(b) by 0 days.

(21) Appl. No.: 13/932,883

(22) Filed: Jul. 1, 2013

(65) Prior Publication Data
US 2013/0289142 A1 Oct. 31, 2013

Related U.S. Application Data

(63) Continuation of application No. PCT/US2011/067998, filed on Dec. 29, 2011.

(60) Provisional application No. 61/428,147, filed on Dec. 29, 2010.

(51) Int. Cl.
*G01N 30/72* (2006.01)
*G01N 33/68* (2006.01)
*G01N 33/574* (2006.01)
*G01N 33/74* (2006.01)

(52) U.S. Cl.
CPC .......... *G01N 33/6893* (2013.01); *G01N 33/574* (2013.01); *G01N 33/6848* (2013.01); *G01N 33/74* (2013.01); *G01N 2333/485* (2013.01); *G01N 2333/71* (2013.01); *G01N 2333/9121* (2013.01)

(58) Field of Classification Search
CPC . G01N 33/574; C07K 14/4748; C12Q 1/6886
See application file for complete search history.

(56) References Cited

U.S. PATENT DOCUMENTS

| 7,501,286 B2 | 3/2009 | Gygi et al. | |
|---|---|---|---|
| 2008/0108795 A1 | 5/2008 | Guo et al. | |
| 2008/0124345 A1* | 5/2008 | Rothe et al. | 424/174.1 |
| 2009/0099340 A1 | 4/2009 | Guo et al. | |
| 2009/0156475 A1* | 6/2009 | Rikova et al. | 514/12 |
| 2009/0215636 A1 | 8/2009 | Krizman et al. | |
| 2009/0215812 A1 | 8/2009 | Bedrosian et al. | |

FOREIGN PATENT DOCUMENTS

| WO | WO 2006/068640 | 6/2006 | |
|---|---|---|---|
| WO | WO 2007/092932 | 8/2007 | |
| WO | WO 2009/002946 | * 12/2008 | G01N 33/53 |
| WO | 2010083252 A2 | 7/2010 | |

OTHER PUBLICATIONS

International Search Report of PCT/US2011/067998; mailed May 8, 2012.
Ballif B et al.: "Quantitative phosphorylation profiling of the ERK/p90 ribosomal S6 kinase-signaling cassette and its targets, the tuberous sclerosis tumor suppressors," PNAS, vol. 102, No. 3, Jan. 18, 2005, pp. 667-672.
Gerber S et al.: Absolute quantification of proteins and phosphoproteins from cell lysates by tandem MS,: PNAS, vol. 100, No. 12, Jun. 10, 2003, pp. 6940-6945.
Guzel et al.: "Multiple Reaction Monitoring Assay for Pre-eclampsia Related Calcyclin Peptides in Formalin Fixed Paraffin Embedded Placenta," Journal of Proteome Research, Oct. 26, 2010, pp. A-I.
Hawkridge A et al.: "Quantitative mass spectral evidence for the absence of circulating brain natriuretic peptide (BNP-32) in severe human heart failure," PNAS, vol. 102, No. 48, Nov. 29, 2005, pp. 17442-17447.
Kocher, et al., "High Precision Quantitative Proteomics Using iTRAQ on an LTQ Orbitrap: A New Mass Spectrometric Method Combining the Benefits of All", Journal of Proteomic Research, vol. 8., No. 10, Oct. 2, 2009 pp. 4743-4752.
Partial European Search Report for Application EP11852979.1; Mail Date Mar. 25, 2015; 8 pages.
Rush, J. et al., "Immunoaffinity profiling of tyrosine phosphorylation in cancer cells.", Nature Biotechnology, Nature Publishing Group, New York, NY, US, vol. 23, No. 1, Jan. 1, 2005, pp. 94-101.
Becker, K-F et al.: "Quantitative protein analysis from formalin-fixed tissues: implications for translational clinical research and nanoscale molecular diagnosis," Journal of Pathology, John Wiley & Sons Ltd, GB, vol. 211, No. 3, Feb. 1, 2007, pp. 370-378.

(Continued)

*Primary Examiner* — Brad Duffy
*Assistant Examiner* — Nelson B Moseley, II
(74) *Attorney, Agent, or Firm* — Perkins Coie LLC

(57) ABSTRACT

The current disclosure provides for specific peptides, and derived ionization characteristics of the peptides, from the Receptor Tyrosine-Protein Kinase erbB-3, or Her3, that are particularly advantageous for quantifying the Her3 protein directly in biological samples that have been fixed in formalin by the method of Selected Reaction Monitoring (SRM) mass spectrometry, or what can also be termed as Multiple Reaction Monitoring (MRM) mass spectrometry. Such biological samples are chemically preserved and fixed wherein said biological sample is selected from tissues and cells treated with formaldehyde containing agents/fixatives including formalin-fixed tissue/cells, formalin-fixed/paraffin embedded (FFPE) tissue/cells, FFPE tissue blocks and cells from those blocks, and tissue culture cells that have been formalin fixed and or paraffin embedded. A protein sample is prepared from said biological sample using the Liquid Tissue™ reagents and protocol and the Her3 protein is quantitated in the Liquid Tissue™ sample by the method of SRM/MRM mass spectrometry by quantitating in the protein sample at least one or more of the peptides described. These peptides can be quantitated if they reside in a modified or an unmodified form. An example of a modified form of a Her3 peptide is phosphorylation of a tyrosine, threonine, serine, and/or other amino acid residues within the peptide sequence.

21 Claims, No Drawings

(56) References Cited

OTHER PUBLICATIONS

Niroshini, et al., "Initial Development and Validation of a Novel Extraction Method for Quantitative Mining of the Formalin-Fixed, Paraffin-Embedded Tissue Proteome for Biomarker Investigations", Journal of Proteome Research, vol. 10., No. 2., Nov. 30, 2010 pp. 896-906.

Bagnato, C. et al.: "Proteomic Analysis of Human Coronary Atherosclerotic Plaque: A Feasibility Study of Direct Tissue Proteomics by Liquid-Chromatography and Tandem Mass Spectrometry," The American Society for Biochemistry and Molecular Biology, Inc., Mar. 27, 2007.

Williamson, et al.: "Automated Identification and Quantification of Protein Phosphorylation Sites by LC/MS on a Hybrid Triple Quadrupole Linear Ion Trap Mass Spectrometer," The American Society for Biochemistry and Molecular Biology, Inc., Jun. 23, 2008, pp. 337-346.

Taylor, P. et al.: "PP118 Detection and quantification of EGF receptor Phosphorylation in formalin-fixed tumor sections by selected/multiple reaction monitoring mass spectrometry," European Journal of Cancer. Supplement, Pergamon, Oxford, GB, vol. 7, No. 4, Oct. 1, 2009 p. 31.

* cited by examiner

SEQUENCE LISTING

<160> NUMBER OF SEQ ID NOS: 10

<210> SEQ ID NO 1
<211> LENGTH: 8
<212> TYPE: PRT

```
<213> ORGANISM: Artificial Sequence
<220> FEATURE:
<223> OTHER INFORMATION: Her3 Peptide

<400> SEQUENCE: 1

Glu Leu Ala Asn Glu Phe Thr Arg
1               5

<210> SEQ ID NO 2
<211> LENGTH: 10
<212> TYPE: PRT
<213> ORGANISM: Artificial Sequence
<220> FEATURE:
<223> OTHER INFORMATION: Her3 Peptide

<400> SEQUENCE: 2

Leu Ala Glu Val Pro Asp Leu Leu Glu Lys
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Her3 Peptide

<400> SEQUENCE: 3

Ile Tyr Ile Ser Ala Asn Arg
1               5

<210> SEQ ID NO 4
<211> LENGTH: 16
<212> TYPE: PRT
<213> ORGANISM: Artificial Sequence
<220> FEATURE:
<223> OTHER INFORMATION: Her3 Peptide
<220> FEATURE:
<221> NAME/KEY: MOD_RES
<222> LOCATION: (14)..(14)
<223> OTHER INFORMATION: PHOSPHORYLATION

<400> SEQUENCE: 4

Ala Phe Gln Gly Pro Gly His Gln Ala Pro His Val His Tyr Ala Arg
1               5                   10                  15

<210> SEQ ID NO 5
<211> LENGTH: 18
<212> TYPE: PRT
<213> ORGANISM: Artificial Sequence
<220> FEATURE:
<223> OTHER INFORMATION: Her3 Peptide
<220> FEATURE:
<221> NAME/KEY: MOD_RES
<222> LOCATION: (14)..(14)
<223> OTHER INFORMATION: PHOSPHORYLATION

<400> SEQUENCE: 5

Ser Leu Glu Ala Thr Asp Ser Ala Phe Asp Asn Pro Asp Tyr Trp His
1               5                   10                  15

Ser Arg

<210> SEQ ID NO 6
<211> LENGTH: 26
<212> TYPE: PRT
<213> ORGANISM: Artificial Sequence
<220> FEATURE:
<223> OTHER INFORMATION: Her3 Peptide
<220> FEATURE:
```

```
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (22)..(22)
<223> OTHER INFORMATION: PHOSPHORYLATION

<400> SEQUENCE: 6

Asp Gly Gly Gly Pro Gly Gly Asp Tyr Ala Ala Met Gly Ala Cys Pro
1               5                   10                  15

Ala Ser Glu Gln Gly Tyr Glu Glu Met Arg
            20                  25

<210> SEQ ID NO 7
<211> LENGTH: 26
<212> TYPE: PRT
<213> ORGANISM: Artificial Sequence
<220> FEATURE:
<223> OTHER INFORMATION: Her3 Peptide
<220> FEATURE:
<221> NAME/KEY: MOD_RES
<222> LOCATION: (9)..(9)
<223> OTHER INFORMATION: PHOSPHORYLATION

<400> SEQUENCE: 7

Asp Gly Gly Gly Pro Gly Gly Asp Tyr Ala Ala Met Gly Ala Cys Pro
1               5                   10                  15

Ala Ser Glu Gln Gly Tyr Glu Glu Met Arg
            20                  25

<210> SEQ ID NO 8
<211> LENGTH: 26
<212> TYPE: PRT
<213> ORGANISM: Artificial Sequence
<220> FEATURE:
<223> OTHER INFORMATION: Her3 Peptide
<220> FEATURE:
<221> NAME/KEY: MOD_RES
<222> LOCATION: (22)..(22)
<223> OTHER INFORMATION: PHOSPHORYLATION

<400> SEQUENCE: 8

Asp Gly Gly Gly Pro Gly Gly Asp Tyr Ala Ala Met Gly Ala Cys Pro
1               5                   10                  15

Ala Ser Glu Gln Gly Tyr Glu Glu Met Arg
            20                  25

<210> SEQ ID NO 9
<211> LENGTH: 26
<212> TYPE: PRT
<213> ORGANISM: Artificial Sequence
<220> FEATURE:
<223> OTHER INFORMATION: Her3 Peptide

<400> SEQUENCE: 9

Asp Gly Gly Gly Pro Gly Gly Asp Tyr Ala Ala Met Gly Ala Cys Pro
1               5                   10                  15

Ala Ser Glu Gln Gly Tyr Glu Glu Met Arg
            20                  25

<210> SEQ ID NO 10
<211> LENGTH: 16
<212> TYPE: PRT
<213> ORGANISM: Artificial Sequence
<220> FEATURE:
<223> OTHER INFORMATION: Her3 Peptide
```

```
<400> SEQUENCE: 10

Ala Asn Asp Ala Leu Gln Val Leu Gly Leu Leu Phe Ser Leu Ala Arg
1               5                   10                  15
```

US 9,128,102 B2

HER3 PROTEIN SRM/MRM ASSAY

This application is a continuation of International Application No. PCT/US2011/067998, filed Dec. 29, 2011, which claims the benefit of U.S. Provisional Application No. 61/428,145, filed Dec. 29, 2010, both of which are entitled "Her3 Protein SRM/MRM Assay," the contents of each of which are hereby incorporated by reference in their entireties. This application also contains a sequence listing submitted electronically via EFS-web, which serves as both the paper copy and the computer readable form (CRF) and consists of a file entitled "01152 8021 US01 Seq Listing", which was created on Jul. 1, 2013, which is 3,340 bytes in size, and which is also incorporated by reference in its entirety.

INTRODUCTION

Specific peptides derived from subsequences of the Receptor Tyrosine-Protein Kinase erbB-3 protein and which will be referred to as Her3, and which can also be referred to as the proto-oncogene-like protein c-ErbB-3, the tyrosine kinase-type cell surface receptor Her3, and the ERBB3 protein are provided. The peptide sequence and fragmentation/transition ions for each peptide are particularly useful in a mass spectrometry-based Selected Reaction Monitoring (SRM) assay(s), which can also be referred to as a Multiple Reaction Monitoring (MRM) assay(s), hereinafter referred to as SRM/MRM assay(s). The use of one such peptide for SRM/MRM quantitative analysis of the Her3 protein is described.

This SRM/MRM assay can be used to detect the presence and to measure relative or absolute quantitative levels of one or more of the specific peptides from the Her3 protein and therefore provide a means of measuring the amount of the Her3 protein in a given protein preparation obtained from a biological sample by mass spectrometry.

The SRM/MRM assays described herein can measure Her3 peptides directly in complex protein lysate samples prepared from cells procured from patient tissue samples, such as formalin fixed cancer patient tissue. Methods of preparing protein samples from formalin-fixed tissue are described in U.S. Pat. No. 7,473,532, the contents of which are hereby incorporated by references in their entirety. The methods described in that patent may conveniently be carried out using Liquid Tissue™ reagents and protocol available from Expression Pathology Inc. (Rockville, Md.).

Formaldehyde/formalin fixation of tissues surgically removed from cancer patients is the accepted convention in pathology practice. As a result, formaldehyde/formalin fixed paraffin embedded tissue is the most widely available form of tissues from those patients. Formaldehyde/formalin fixation typically employs aqueous solutions of formaldehyde referred to as formalin. "100%" formalin consists of a saturated solution of formaldehyde (about 40% formaldehyde by volume or 37% by mass) in water, with a small amount of stabilizer, usually methanol to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay can be used to correlate accurate and precise quantitative levels of the Her3 protein within the specific tissue samples (e.g., cancer tissue sample) of the patient or subject from whom the tissue (biological sample) was collected and preserved. This not only provides diagnostic information about the cancer, but also permits a physician or other medical professional to determine appropriate therapy for the patient. Such an assay that provides diagnostically and therapeutically important information about levels of protein expression in a diseased tissue or other patient sample is termed a companion diagnostic assay. For example, such an assay can be designed to diagnose the stage or degree of a cancer and determine a therapeutic agent to which a patient is most likely to respond.

SUMMARY

The assays described herein measure relative or absolute levels of specific unmodified peptides from the Her3 protein and also can measure absolute or relative levels of specific modified peptides from the Her3 protein. Examples of modifications include phosphorylated amino acid residues and glycosylated amino acid residues that are present on the peptides.

Relative quantitative levels of the Her3 protein are determined by the SRM/MRM methodology, for example by comparing SRM/MRM signature peak areas (e.g., signature peak area or integrated fragment ion intensity) of an individual Her3 peptide in different samples (e.g., a control sample and an sample prepared from a patient's tissue). Alternatively, it is possible to compare multiple SRM/MRM signature peak areas for multiple Her3 signature peptides, where each peptide has its own specific SRM/MRM signature peak, to determine the relative Her3 protein content in one biological sample with the Her3 protein content in one or more additional or different biological samples. In this way, the amount of a particular peptide, or peptides, from the Her3 protein, and therefore the amount of the Her3 protein, is determined relative to the same Her3 peptide, or peptides, across 2 or more biological samples under the same experimental conditions. In addition, relative quantitation can be determined for a given peptide, or peptides, from the Her3 protein within a single sample by comparing the signature peak area for that peptide by SRM/MRM methodology to the signature peak area for another and different peptide, or peptides, from a different protein, or proteins, within the same protein preparation from the biological sample. In this way, the amount of a particular peptide from the Her3 protein, and therefore the amount of the Her3 protein, is determined relative one to another within the same sample. These approaches generate quantitation of an individual peptide, or peptides, from the Her3 protein to the amount of another peptide, or peptides, between samples and within samples wherein the amounts as determined by peak area are relative one to another, regardless of the absolute weight to volume or weight to weight amounts of the Her3 peptide in the protein preparation from the biological sample. Relative quantitative data about individual signature peak areas between different samples are normalized to the amount of protein analyzed per sample. Relative quantitation can be performed across many peptides from multiple proteins and the Her3 protein simultaneously in a single sample and/or across many samples to gain insight into relative protein amounts, one peptide/protein with respect to other peptides/proteins.

Absolute quantitative levels of the Her3 protein are determined by, for example, the SRM/MRM methodology whereby the SRM/MRM signature peak area of an individual peptide from the Her3 protein in one biological sample is compared to the SRM/MRM signature peak area of a known amount of a "spiked" internal standard. In one embodiment, the internal standard is a synthetic version of the same exact Her3 peptide that contains one or more amino acid residues labeled with one or more heavy isotopes. Such isotope labeled internal standards are synthesized so mass spectrometry analysis generates a predictable and consistent SRM/MRM signature peak that is different and distinct from the native Her3 peptide signature peak and which can be used as a comparator peak. Thus when the internal standard is spiked in known amounts into a protein or peptide preparation from a biological sample in known amounts and analyzed by mass spectrometry, the SRM/MRM signature peak area of the native peptide is compared to the SRM/MRM signature peak area of the internal standard peptide, and this numerical comparison indicates either the absolute molarity and/or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in entire cohorts of individual samples.

The SRM/MRM assay method can be used to aid diagnosis of the stage of cancer, for example, directly in patient-derived tissue, such as formalin fixed tissue, and to aid in determining which therapeutic agent would be most advantageous for use in treating that patient. Cancer tissue that is removed from a patient either through surgery, such as for therapeutic removal of partial or entire tumors, or through biopsy procedures conducted to determine the presence or absence of suspected disease, is analyzed to determine whether or not a specific protein, or proteins, and which forms of proteins, are present in that patient tissue. Moreover, the expression level of a protein, or multiple proteins, can be determined and compared to a "normal" or reference level found in healthy tissue. Normal or reference levels of proteins found in healthy tissue may be derived from, for example, the relevant tissues of one or more individuals that do not have cancer. Alternatively, normal or reference levels may be obtained for individuals with cancer by analysis of relevant tissues not affected by the cancer.

Assays of protein levels (e.g., Her3 levels) can also be used to diagnose the stage of cancer in a patient or subject diagnosed with cancer by employing the Her3 levels. Levels or amounts of proteins or peptides can be defined as the quantity expressed in moles, mass or weight of a protein or peptide determined by the SRM/MRM assay. The level or amount may be normalized to the total level or amount of protein or another component in the lysate analyzed (e.g., expressed in micromoles/microgram of protein or micrograms/microgram of protein). In addition, the level or amount of a protein or peptide may be determined on volume basis, expressed, for example, in micromolar or nanograms/microliter. The level or amount of protein or peptide as determined by the SRM/MRM assay can also be normalized to the number of cells analyzed. Information regarding Her3 can thus be used to aid in determining stage or grade of a cancer by correlating the level of the Her3 protein (or fragment peptides of the Her3 protein) with levels observed in normal tissues.

Once the stage and/or grade, and/or Her3 protein expression characteristics of the cancer has been determined, that information can be matched to a list of therapeutic agents (chemical and biological) developed to specifically treat cancer tissue that is characterized by, for example, abnormal expression of the protein or protein(s) (e.g., Her3) that were assayed. Matching information from a Her3 protein assay to a list of therapeutic agents that specifically targets, for example, the Her3 protein or cells/tissue expressing the protein, defines what has been termed a personalized medicine approach to treating disease. The assay methods described herein form the foundation of a personalized medicine approach by using analysis of proteins from the patient's own tissue as a source for diagnostic and treatment decisions.

Certain embodiments of the invention are described below.

1. A method for measuring the level of Receptor Tyrosine-Protein Kinase erbB-3 (Her3) protein in a biological sample, comprising detecting and/or quantifying the amount of one or more modified or unmodified Her3 fragment peptides in a protein digest prepared from said biological sample using mass spectrometry; and calculating the level of modified or unmodified Her3 protein in said sample; and wherein said level is a relative level or an absolute level.
2. The method of embodiment 1, further comprising the step of fractionating said protein digest prior to detecting and/or quantifying the amount of one or more modified or unmodified Her3 fragment peptides.
3. The method of embodiment 2, wherein said fractionating step is selected from the group consisting of gel electrophoresis, liquid chromatography, capillary electrophoresis, nano-reversed phase liquid chromatography, high performance liquid chromatography, or reverse phase high performance liquid chromatography.
4. The method of any of embodiments 1-3, wherein said protein digest of said biological sample is prepared by the Liquid Tissue™ protocol.
5. The method of any of embodiments 1-3, wherein said protein digest comprises a protease digest.
6. The method of embodiment 5, wherein said protein digest comprises a trypsin digest.
7. The method of any of embodiments 1-6, wherein said mass spectrometry comprises tandem mass spectrometry, ion trap mass spectrometry, triple quadrupole mass spectrometry, MALDI-TOF mass spectrometry, MALDI mass spectrometry, and/or time of flight mass spectrometry.
8. The method of embodiment 7, wherein the mode of mass spectrometry used is Selected Reaction Monitoring (SRM), Multiple Reaction Monitoring (MRM), and/or multiple Selected Reaction Monitoring (mSRM).
9. The method of any of embodiments 1 to 8, wherein the Her3 fragment peptide comprises an amino acid sequence as set forth as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.
10. The method of any of embodiments 1-9, wherein the biological sample is a blood sample, a urine sample, a serum sample, an ascites sample, a sputum sample, lymphatic fluid, a saliva sample, a cell, or a solid tissue.
11. The method of embodiment 10, wherein the tissue is formalin fixed tissue.
12. The method of embodiment 10 or 11, wherein the tissue is paraffin embedded tissue.
13. The method of embodiment 10, wherein the tissue is obtained from a tumor.
14. The method of embodiment 13, wherein the tumor is a primary tumor.
15. The method of embodiment 13, wherein the tumor is a secondary tumor.

16. The method of any of embodiments 1-15, further comprising quantifying a modified or unmodified Her3 fragment peptide.

17. The method of embodiment 16, wherein quantifying the Her3 fragment peptide comprises comparing an amount of one or more Her3 fragment peptides comprising an amino acid sequence of about 8 to about 45 amino acid residues of Her3 as shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10 in one biological sample to the amount of the same Her3 fragment peptide in a different and separate biological sample.

18. The method of embodiment 17, wherein quantifying one or more Her3 fragment peptides comprises determining the amount of the each of the Her3 fragment peptides in a biological sample by comparison to an added internal standard peptide of known amount, wherein each of the Her3 fragment peptides in the biological sample is compared to an internal standard peptide having the same amino acid sequence.

19. The method of embodiment 18, wherein the internal standard peptide is an isotopically labeled peptide.

20. The method of embodiment 19, wherein the isotopically labeled internal standard peptide comprises one or more heavy stable isotopes selected from 18O, 17O, 34S, 15N, 13C, 2H or combinations thereof.

21. The method of any of embodiments 1-20, wherein detecting and/or quantifying the amount of one or more modified or unmodified Her3 fragment peptides in the protein digest indicates the presence of modified or unmodified Her3 protein and an association with cancer in the subject.

22. The method of embodiment 21, further comprising correlating the results of said detecting and/or quantifying the amount of one or more modified or unmodified Her3 fragment peptides, or the level of said Her3 protein to the diagnostic stage/grade/status of the cancer.

23. The method of embodiment 22, wherein correlating the results of said detecting and/or quantifying the amount of one or more modified or unmodified Her3 fragment peptides, or the level of said Her3 protein to the diagnostic stage/grade/status of the cancer is combined with detecting and/or quantifying the amount of other proteins or peptides from other proteins in a multiplex format to provide additional information about the diagnostic stage/grade/status of the cancer.

24. The method of any one of embodiments 1-23, further comprising selecting for the subject from which said biological sample was obtained a treatment based on the presence, absence, or amount of one or more Her3 fragment peptides or the level of Her3 protein.

25. The method of any one of embodiments 1-24, further comprising administering to the patient from which said biological sample was obtained a therapeutically effective amount of a therapeutic agent, wherein the therapeutic agent and/or amount of the therapeutic agent administered is based upon amount of one or more modified or unmodified Her3 fragment peptides or the level of Her3 protein.

26. The method of embodiments 24 and 25, wherein therapeutic agents bind the Her3 protein and/or inhibit its biological activity.

27. The method of embodiments 1-26, wherein the biological sample is formalin fixed tumor tissue that has been processed for quantifying the amount of one or more modified or unmodified Her3 fragment peptides employing the Liquid Tissue™ protocol and reagents.

28. The method of any of embodiments 1-27, wherein said one or more modified or unmodified Her3 fragment peptides is two or more, three or more, four or more, five or more, six or more, eight or more, or nine or more of the peptides in Table 1.

29. The method of any of embodiments 1-28, comprising quantifying the amount of the peptide in Table 2.

30. A composition comprising one or more, two or more, three or more, four or more, five or more, six or more, eight or more, or nine or more of the peptides in Table 1 or antibodies thereto.

31. The composition of embodiment 30 comprising the peptide of Table 2 or an antibody thereto.

32. The composition of embodiments 30 or 31, wherein said composition is substantially pure or free of other cellular components selected from any combination of other proteins, membranes lipids and/or nucleic acids.

33. The composition of any of embodiment 30-32, wherein said peptides are isotopically labeled internal standard peptides that comprises one or more, two or more, or three or more, heavy stable isotopes selected from 18O, 17O, 34S, 15N, 13C, 2H or combinations thereof.

34. The method of embodiments 1-29, further comprising assessing and/or determining the level (amount) or sequence of one, two, three, four or more nucleic acids in said protein digest.

35. The method of claim 34, wherein said nucleic acids have a length greater than about 15, 20, 25, 30, 35, 40, 50, 60, 75, or 100 nucleotides in length.

36. The method of claim 35, wherein said nucleic acids have a length less than about 150, 200, 250, 300, 350, 400, 500, 600, 750, 1,000, 2,000, 4,000, 5,000, 7,500, 10,000, 15,000, or 20,000 nucleotides in length.

37. The method of any of embodiments 34-36, wherein assessing and/or determining the level (amount) or sequence comprises, determining either the sequence of nucleotides in the nucleic acids and/or a characteristic of the nucleic acids by any one or more of: nucleic acid sequencing, conducting restriction fragment polymorphism analysis, nucleic acid hybridization identification of one or more deletions and/or insertions, and/or determining the presence of mutations, including but not limited to, single base pair polymorphisms, transitions and/or transversions.

DETAILED DESCRIPTION

In principle, any predicted peptide derived from Her3 protein, prepared for example by digesting with a protease of known specificity (e.g. trypsin), can be used as a surrogate reporter to determine the abundance of Her3 protein in a sample using a mass spectrometry-based SRM/MRM assay. Similarly, any predicted peptide sequence containing an amino acid residue at a site that is known to be potentially modified in Her3 protein also might potentially be used to assay the extent of modification of Her3 protein in a sample.

Her3 fragment peptides may be generated by a variety of means including by the use of the Liquid Tissue™ protocol provided in U.S. Pat. No. 7,473,532. The Liquid Tissue™ protocol and reagents are capable of producing peptide samples suitable for mass spectroscopic analysis from formalin fixed paraffin embedded tissue by proteolytic digestion of the proteins in the tissue/biological sample. In the Liquid Tissue™ protocol the tissue/biological is maintained at elevated temperatures in a buffer for an extended period of time (e.g., from about 80° C. to about 100° C. for a period of time from about 10 minutes to about 4 hours) to reverse or release protein cross-linking. The buffer employed is a neutral buffer, (e.g., a Tris-based buffer, or a buffer containing a detergent) and advantageously is a buffer that does not interfere with mass spectrometric analysis. Next the tissue/biological sample is treated with one or more proteases, including but not limited to trypsin, chymotrypsin, pepsin, and endoproteinase Lys-C for a time sufficient to disrupt the tissue and cellular structure of said biological sample and to liquefy said sample (e.g., a period of time from 30 minutes to 24 hours at a temperature from 37° C. to 65° C.). The result of the heating and proteolysis is a liquid, soluble, dilutable biomolecule lysate.

Once lysates are prepared peptides in the samples may subject to a variety of techniques that facilitate their analysis and measurement by mass spectrometry. In one embodiment, the peptides may be separated by an affinity technique, such as for example immunologically-based purification (e.g., immunoaffinity chromatography), chromatography on ion selective media, or if the peptides are modified, by separation using appropriate media, such as lectins for separation of carbohydrate modified peptides. In one embodiment, the SIS-CAPA method, which employs immunological separation of peptides prior to mass spectrometric analysis is employed. The SISCAPA technique is described, for example, in U.S. Pat. No. 7,632,686. In other embodiments, lectin affinity methods (e.g., affinity purification and/or chromatography may be used to separate peptides from a lysate prior to analysis by mass spectrometry. Methods for separation of groups of peptides, including lectin-based methods, are described, for example, in Geng et al., J. Chromatography B, 752:293-306 (2001). Immunoaffinity chromatography techniques, lectin affinity techniques and other forms of affinity separation and/or chromatography (e.g., reverse phase, size based separation, ion exchange) may be used in any suitable combination to facilitate the analysis of peptides by mass spectrometry.

Surprisingly, it was found that many potential peptide sequences from the Her3 protein are unsuitable or ineffective for use in mass spectrometry-based SRM/MRM assays for reasons that are not immediately evident. In particular it was found that many tryptic peptides from the Her3 protein could not be detected efficiently or at all in a Liquid Tissue lysate from formalin fixed, paraffin embedded tissue. As it was not possible to predict the most suitable peptides for MRM/SRM assay, it was necessary to experimentally identify modified and unmodified peptides in actual Liquid Tissue™ lysates to develop a reliable and accurate SRM/MRM assay for the Her3 protein. While not wishing to be bound by any theory, it is believed that some peptides might, for example, be difficult to detect by mass spectrometry as they do not ionize well or produce fragments distinct from other proteins, peptides may also fail to resolve well in separation (e.g., liquid chromatography), or adhere to glass or plastic ware. Accordingly, those peptides from the Her3 protein that can be detected in a Liquid Tissue lysate (e.g., the peptides in Tables 1 and 2) prepared from a formalin fixed tissue sample are the peptides for which SRM/MRM assays can be employed in a Her3 SRM/MRM assay.

Her3 peptides found in various embodiments of this disclosure (e.g., Tables 1 and 2) were derived from the Her3 protein by protease digestion of all the proteins within a complex Liquid Tissue™ lysate prepared from cells procured from formalin fixed cancer tissue. Unless noted otherwise, in each instance the protease was trypsin. The Liquid Tissue™ lysate was then analyzed by mass spectrometry to determine those peptides derived from the Her3 protein that are detected and analyzed by mass spectrometry. Identification of a specific preferred subset of peptides for mass-spectrometric analysis is based on: 1) experimental determination of which peptide or peptides from a protein ionize in mass spectrometry analyses of Liquid Tissue™ lysates; and 2) the ability of the peptide to survive the protocol and experimental conditions used in preparing a Liquid Tissue™ lysate. This latter property extends not only to the amino acid sequence of the peptide but also to the ability of a modified amino acid residue within a peptide to survive in modified form during the sample preparation.

TABLE 1

| Peptide | Peptide Sequence |
| --- | --- |
| SEQ ID NO: 1 | ELANEFTR |
| SEQ ID NO: 2 | LAEVPDLLEK |
| SEQ ID NO: 3 | IYISANR |
| SEQ ID NO: 4 | AFQGPGHQAPHVHY[Phosphoryl]AR |
| SEQ ID NO: 5 | SLEATDSAFDNPDY[Phosphoryl]WHSR |
| SEQ ID NO: 6 | DGGGPGGDY[Phosphoryl]AAMGACPASEQGY[Phosphoryl]EEMR |
| SEQ ID NO: 7 | DGGGPGGDY[Phosphoryl]AAMGACPASEQGYEEMR |
| SEQ ID NO: 8 | DGGGPGGDYAAMGACPASEQGY[Phosphoryl]EEMR |
| SEQ ID NO: 9 | DGGGPGGDYAAMGACPASEQGYEEMR |
| SEQ ID NO: 10 | ANDALQVLGLLFSLAR |

TABLE 2

| SEQ ID | Peptide sequence | Mono Isotopic Mass | Precursor Charge State | Precursor m/z | Transition m/z | Ion Type |
|---|---|---|---|---|---|---|
| SEQ ID NO: 10 | ANDALQVLOLLFSLAR | 1700.96938 | 2 | 850.9879761 | 876.5296 | y8 |
| | | | 2 | | 989.6137 | y9 |
| | | | 2 | | 1088.682 | y10 |
| | | | 2 | | 1216.741 | y11 |
| | | | 2 | | 1329.825 | y12 |
| | | | 2 | | 1400.862 | y13 |

Protein lysates from cells procured directly from formalin (formaldehyde) fixed tissue were prepared using the Liquid Tissue™ reagents and protocol that entails collecting cells into a sample tube via tissue microdissection followed by heating the cells in the Liquid Tissue™ buffer for an extended period of time. Once the formalin-induced cross linking has been negatively affected, the tissue/cells are then digested to completion in a predictable manner using a protease, as for example including but not limited to the protease trypsin. Each protein lysate is turned into a collection of peptides by digestion of intact polypeptides with the protease. Each Liquid Tissue™ lysate was analyzed (e.g., by ion trap mass spectrometry) to perform multiple global proteomic surveys of the peptides where the data was presented as identification of as many peptides as could be identified by mass spectrometry from all cellular proteins present in each protein lysate. An ion trap mass spectrometer or another form of a mass spectrometer that is capable of performing global profiling for identification of as many peptides as possible from a single complex protein/peptide lysate is employed. Ion trap mass spectrometers however may be the best type of mass spectrometer for conducting global profiling of peptides. Although SRM/MRM assay can be developed and performed on any type of mass spectrometer, including a MALDI, ion trap, or triple quadrupole, the most advantageous instrument platform for SRM/MRM assay is often considered to be a triple quadrupole instrument platform.

Once as many peptides as possible were identified in a single MS analysis of a single lysate under the conditions employed, then that list of peptides was collated and used to determine the proteins that were detected in that lysate. That process was repeated for multiple Liquid Tissue™ lysates, and the very large list of peptides was collated into a single dataset. That type of dataset can be considered to represent the peptides that can be detected in the type of biological sample that was analyzed (after protease digestion), and specifically in a Liquid Tissue™ lysate of the biological sample, and thus includes the peptides for specific proteins, such as for example the Her3 protein.

In one embodiment, the Her3 tryptic peptides identified as useful in the determination of absolute or relative amounts of the Her3 receptor include one or more, two or more, three or more, four or more, five or more, six or more, eight or more, or nine or more of the peptides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, each of which are listed in Table 1. Each of those peptides was detected by mass spectrometry in Liquid Tissue™ lysates prepared from formalin fixed, paraffin embedded tissue. Thus, each of the peptides in Table 1, or any combination of those peptides (e.g., one or more, two or more, three or more, four or more, five or more, six or more, eight or more, or nine or more of those peptides recited in Table 1, and particularly combinations with the peptide found in Table 2) are candidates for use in quantitative SRM/MRM assay for the Her3 protein in human biological samples, including directly in formalin fixed patient tissue.

The Her3 tryptic peptides listed in Table 1 include those detected from multiple Liquid Tissue™ lysates of multiple different formalin fixed tissues of different human organs including prostate, colon, and breast. Each of those peptides is considered useful for quantitative SRM/MRM assay of the Her3 protein in formalin fixed tissue. Further data analysis of these experiments indicated no preference is observed for any specific peptides from any specific organ site. Thus, each of these peptides is believed to be suitable for conducting SRM/MRM assays of the Her3 protein on a Liquid Tissue™ lysate from any formalin fixed tissue originating from any biological sample or from any organ site in the body.

In one embodiment the peptides in Table 1, or any combination of those peptides (e.g., one or more, two or more, three or more, four or more, five or more, six or more, eight or more, or nine or more of those peptides recited in Table 1, and particularly combinations with the peptide also found in Table 2) are assayed by methods that do not rely upon mass spectroscopy, including, but not limited to, immunological methods (e.g., Western blotting or ELISA). Regardless of how information directed to the amount of the peptide(s) (absolute or relative) is obtained, the information may be employed in any of the methods described herein, including indicating (diagnosing) the presence of cancer in a subject, determining the stage/grade/status of the cancer, providing a prognosis, or determining the therapeutics or treatment regimen for a subject/patient.

Embodiments of the present disclosure include compositions comprising one or more, two or more, three or more, four or more, five or more, six or more, eight or more, or nine or more of the peptides in Table 1. In some embodiments, the compositions comprise the peptide in Table 2. Compositions comprising peptides may include one or more, two or more, three or more, four or more, five or more, six or more, eight or more, or nine or more peptides that are isotopically labeled. Each of the peptides may be labeled with one or more isotopes selected independently from the group consisting of: $^{18}O$, $^{17}O$, $^{34}S$, $^{15}N$, $^{13}C$, $^{2}H$ or combinations thereof. Compositions comprising peptides from the Her3 protein, whether isotope labeled or not, do not need to contain all of the peptides from that protein (e.g., a complete set of tryptic peptides). In some embodiments the compositions do not contain one or more, two or more, three or more, four or more, five or more, six or more, eight or more, or nine or more peptides from Her3, and particularly peptides appearing in Table 1 or Table 2. Compositions comprising peptides may be in the form of dried or lyophized materials, liquid (e.g., aqueous) solutions or suspensions, arrays, or blots.

An important consideration when conducting an SRM/MRM assay is the type of instrument that may be employed in the analysis of the peptides. Although SRM/MRM assays can be developed and performed on any type of mass spectrometer, including a MALDI, ion trap, or triple quadrupole, presently the most advantageous instrument platform for SRM/MRM assay is often considered to be a triple quadrupole instrument platform. That type of a mass spectrometer may be considered to be the most suitable instrument for analyzing a single isolated target peptide within a very complex protein lysate that may consist of hundreds of thousands to millions of individual peptides from all the proteins contained within a cell.

In order to most efficiently implement SRM/MRM assay for each peptide derived from the Her3 protein it is desirable to utilize information in addition to the peptide sequence in the analysis. That additional information may be used in directing and instructing the mass spectrometer (e.g. a triple quadrupole mass spectrometer), to perform the correct and focused analysis of specific targeted peptide(s), such that the assay may be effectively performed.

The additional information about target peptides in general, and about specific Her3 peptides, may include one or more of the mono isotopic mass of each peptide, its precursor charge state, the precursor m/z value, the m/z transition ions, and the ion type of each transition ion. Additional peptide information that may be used to develop an SRM/MRM assay for the Her3 protein is shown by example for one (1) of the Her3 peptides from the list in Table 1 and is shown in Table 2. Similar additional information described for this one (1) Her3 peptide shown by example in Table 2 may be prepared, obtained, and applied to the analysis of the other peptides contained in Table 1.

The method described below was used to: 1) identify candidate peptides from the Her3 protein that can be used for a mass spectrometry-based SRM/MRM assay for the Her3 protein, 2) develop individual SRM/MRM assay, or assays, for target peptides from the Her3 protein in order to correlate and 3) apply quantitative assays to cancer diagnosis and/or choice of optimal therapy.

Assay Method

1. Identification of SRM/MRM candidate fragment peptides for the Her3 protein
    a. Prepare a Liquid Tissue™ protein lysate from a formalin fixed biological sample using a protease or proteases, (that may or may not include trypsin), to digest proteins
    b. Analyze all protein fragments in the Liquid Tissue™ lysate on an ion trap tandem mass spectrometer and identify all fragment peptides from the Her3 protein, where individual fragment peptides do not contain any peptide modifications such as phosphorylations or glycosylations
    c. Analyze all protein fragments in the Liquid Tissue™ lysate on an ion trap tandem mass spectrometer and identify all fragment peptides from the Her3 protein that carry peptide modifications such as for example phosphorylated or glycosylated residues
    d. All peptides generated by a specific digestion method from the entire, full length Her3 protein potentially can be measured, but preferred peptides used for development of the SRM/MRM assay are those that are identified by mass spectrometry directly in a complex Liquid Tissue™ protein lysate prepared from a formalin fixed biological sample
    e. Peptides that are specifically modified (phosphorylated, glycosylated, etc.) in patient tissue and which ionize, and thus can be detected, in a mass spectrometer when analyzing a Liquid Tissue™ lysate from a formalin fixed biological sample are identified as candidate peptides for assaying peptide modifications of the Her3 protein 2. Mass Spectrometry Assay for Fragment Peptides from Her3 Protein
    a. SRM/MRM assay on a triple quadrupole mass spectrometer for individual fragment peptides identified in a Liquid Tissue™ lysate is applied to peptides from the Her3 protein
        i. Determine optimal retention time for a fragment peptide for optimal chromatography conditions including but not limited to gel electrophoresis, liquid chromatography, capillary electrophoresis, nano-reversed phase liquid chromatography, high performance liquid chromatography, or reverse phase high performance liquid chromatography
        ii. Determine the mono isotopic mass of the peptide, the precursor charge state for each peptide, the precursor m/z value for each peptide, the m/z transition ions for each peptide, and the ion type of each transition ion for each fragment peptide in order to develop an SRM/MRM assay for each peptide.
        iii. SRM/MRM assay can then be conducted using the information from (i) and (ii) on a triple quadrupole mass spectrometer where each peptide has a characteristic and unique SRM/MRM signature peak that precisely defines the unique SRM/MRM assay as performed on a triple quadrupole mass spectrometer
    b. Perform SRM/MRM analysis so that the amount of the fragment peptide of the Her3 protein that is detected, as a function of the unique SRM/MRM signature peak area from an SRM/MRM mass spectrometry analysis, can indicate both the relative and absolute amount of the protein in a particular protein lysate.
        i. Relative quantitation may be achieved by:
            1. Determining increased or decreased presence of the Her3 protein by comparing the SRM/MRM signature peak area from a given Her3 peptide detected in a Liquid Tissue™ lysate from one formalin fixed biological sample to the same SRM/MRM signature peak area of the same Her3 fragment peptide in at least a second, third, fourth or more Liquid Tissue™ lysates from least a second, third, fourth or more formalin fixed biological samples
            2. Determining increased or decreased presence of the Her3 protein by comparing the SRM/MRM signature peak area from a given Her3 peptide detected in a Liquid Tissue™ lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.
            3. Determining increased or decreased presence of the Her3 protein by comparing the SRM/MRM signature peak area for a given Her3 peptide to the SRM/MRM signature peak areas from other fragment peptides derived from different proteins within the same Liquid Tissue™ lysate from the formalin fixed biological sample in order to normalize changing levels of Her3 protein to levels of other proteins that do not change their levels of expression under various cellular conditions.
4. These assays can be applied to both unmodified fragment peptides and for modified fragment peptides of the Her3 protein, where the modifications include but are not limited to phosphorylation and/or glycosylation, and where the relative levels of modified peptides are determined in the same manner as determining relative amounts of unmodified peptides.
  ii. Absolute quantitation of a given peptide may be achieved by comparing the SRM/MRM signature peak area for a given fragment peptide from the Her3 protein in an individual biological sample to the SRM/MRM signature peak area of an internal fragment peptide standard spiked into the protein lysate from the biological sample
    1. The internal standard is a labeled synthetic version of the fragment peptide from the Her3 protein that is being interrogated. This standard is spiked into a sample in known amounts, and the SRM/MRM signature peak area can be determined for both the internal fragment peptide standard and the native fragment peptide in the biological sample separately, followed by comparison of both peak areas
    2. This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.
3. Apply Fragment Peptide Quantitation to Cancer Diagnosis and Treatment
  a. Perform relative and/or absolute quantitation of fragment peptide levels of the Her3 protein and demonstrate that the previously-determined association, as well understood in the field of cancer, of Her3 protein expression to the stage/grade/status of cancer in patient tumor tissue is confirmed
  b. Perform relative and/or absolute quantitation of fragment peptide levels of the Her3 protein and demonstrate correlation with clinical outcomes from different treatment strategies, wherein this correlation has already been demonstrated in the field or can be demonstrated in the future through correlation studies across cohorts of patients and tissue from those patients. Once either previously established correlations or correlations derived in the future are confirmed by this assay then the assay method can be used to determine optimal treatment strategy.

Assessment of Her3 protein levels in tissues based on analysis of formalin fixed patient-derived tissue can provide diagnostic, prognostic, and therapeutically-relevant information about each particular patient. In one embodiment, this disclosure describes a method for measuring the level of the Her3 protein in a biological sample, comprising detecting and/or quantifying the amount of one or more modified or unmodified Her3 fragment peptides in a protein digest prepared from said biological sample using mass spectrometry; and calculating the level of modified or unmodified Her3 protein in said sample; and wherein said level is a relative level or an absolute level. In a related embodiment, quantifying one or more Her3 fragment peptides comprises determining the amount of the each of the Her3 fragment peptides in a biological sample by comparison to an added internal standard peptide of known amount, wherein each of the Her3 fragment peptides in the biological sample is compared to an internal standard peptide having the same amino acid sequence. In some embodiments the internal standard is an isotopically labeled internal standard peptide comprises one or more heavy stable isotopes selected from $^{18}O$, $^{17}O$, $^{34}S$, $^{15}N$, $^{13}C$, $^{2}H$ or combinations thereof.

The method for measuring the level of the Her3 protein in a biological sample described herein (or fragment peptides as surrogates thereof) may be used as a diagnostic indicator of cancer in a patient or subject. In one embodiment, the results from measurements of the level of the Her3 protein may be employed to determine the diagnostic stage/grade/status of a cancer by correlating (e.g., comparing) the level of Her3 receptor found in a tissue with the level of that protein found in normal and/or cancerous or precancerous tissues.

Because both nucleic acids and protein can be analyzed from the same Liquid Tissue biomolecular preparation it is possible to generate additional information about disease diagnosis and drug treatment decisions from the same sample. For example, the Her3 protein is a tyrosine kinase receptor that is capable of stimulating uncontrolled cell growth (cancer) by activation of specific cell signal protein pathways. If Her3 is expressed by certain cells to at increased levels, when assayed by SRM the data can provide information about the state of the cells and their potential for uncontrolled growth, potential drug resistance and the development of cancers can be obtained. At the same time, information about the status of the Her3 gene and/or the nucleic acids and proteins it encodes (e.g., mRNA molecules and their expression levels or splice variations) can be obtained from nucleic acids present in the same biomolecular preparation. For example information about Her3 and/or one, two, three, four or more additional proteins may be assessed by examining the nucleic acids encoding those proteins. Those nucleic acids can be examined, for example, by one or more sequencing methods, conducting restriction fragment polymorphism analysis, identification of deletions, insertions, and/or determining the presence of mutations, including but not limited to, single base pair polymorphisms, transitions and/or transversions.

The above description and exemplary embodiments of methods and compositions are illustrative of the scope of the present disclosure. Because of variations which will be apparent to those skilled in the art, however, the present disclosure is not intended to be limited to the particular embodiments described above

The invention claimed is:

1. A method for measuring the level of Receptor Tyrosine-Protein Kinase erbB-3 (Her3) protein in a human biological sample of formalin-fixed tissue, comprising detecting and/or quantifying the amount of an Her3 fragment peptide in a protein digest prepared from said human biological sample using mass spectrometry; wherein the Her3 fragment peptide is selected from the group consisting of SEQ ID NO:1, SEQ ID NO:2, SEQ ID NO:3 and SEQ ID NO:10, and calculating the level of Her3 protein in said sample; and wherein said level is a relative level or an absolute level.

2. The method of claim 1, further comprising the step of fractionating said protein digest prior to detecting and/or quantifying the amount of said Her3 fragment peptide.

3. The method of claim 2, wherein said fractionating step is selected from the group consisting of gel electrophoresis, liquid chromatography, capillary electrophoresis, nano-reversed phase liquid chromatography, high performance liquid chromatography, or reverse phase high performance liquid chromatography.

4. The method of claim 1, wherein said protein digest comprises a protease digest.

5. The method of claim 4, wherein said protein digest comprises a trypsin digest.

6. The method of claim 1, wherein said mass spectrometry comprises tandem mass spectrometry, ion trap mass spectrometry, triple quadrupole mass spectrometry, MALDI-TOF mass spectrometry, MALDI mass spectrometry, and/or time of flight mass spectrometry.

7. The method of claim 1, wherein the tissue is paraffin embedded tissue.

8. The method of claim 1, wherein the tissue is obtained from a tumor.

9. The method of claim 1, further comprising quantifying said Her3 fragment peptide.

10. The method of claim 9, wherein quantifying the Her3 fragment peptide comprises comparing an amount of said Her3 fragment peptide in one biological sample to the amount of the same Her3 fragment peptide in a different and separate biological sample.

11. The method of claim 10, wherein quantifying said Her3 fragment peptide comprises determining the amount of the each of the Her3 fragment peptides in a biological sample by comparison to an added internal standard peptide of known amount, wherein said Her3 fragment peptide in the biological sample is compared to an internal standard peptide having the same amino acid sequence, and wherein the internal standard peptide is an isotopically labeled peptide.

12. The method of claim 1, wherein detecting and/or quantifying the amount of said Her3 fragment peptide in the protein digest indicates the presence of Her3 protein and an association with cancer in the subject.

13. The method of claim 12, further comprising correlating the results of said detecting and/or quantifying the amount of said Her3 fragment peptide, or the level of said Her3 protein to the diagnostic stage/grade/status of the cancer.

14. The method of claim 13, wherein correlating the results of said detecting and/or quantifying the amount of said Her3 fragment peptide, or the level of said Her3 protein to the diagnostic stage/grade/status of the cancer is combined with detecting and/or quantifying the amount of other proteins or peptides from other proteins in a multiplex format to provide additional information about the diagnostic stage/grade/status of the cancer.

15. The method of claim 1, further comprising administering to the patient from which said biological sample was obtained a therapeutically effective amount of a therapeutic agent, wherein the therapeutic agent and/or amount of the therapeutic agent administered is based upon amount of said Her3 fragment peptide or the level of Her3 protein.

16. The method of claim 15, wherein said therapeutic agent binds the Her3 protein and/or inhibits its biological activity.

17. The method of claim 1, further comprising assessing and/or determining the level (amount) or sequence of one, two, three, four or more nucleic acids in said protein digest.

18. The method of claim 1, wherein said peptide is SEQ ID NO:1.

19. The method of claim 1, wherein said peptide is SEQ ID NO:2.

20. The method of claim 1, wherein said peptide is SEQ ID NO:3.

21. The method of claim 1, wherein said peptide is SEQ ID NO:10.

* * * * *